United States Patent [19]
LeBoeuf et al.

[11] Patent Number: 5,882,421
[45] Date of Patent: *Mar. 16, 1999

[54] METHOD FOR REDUCING TACINESS OF SOFT ACRYLIC POLYMERS

[75] Inventors: Albert R. LeBoeuf, Fort Worth, Tex.; George Green, St. Louis, Mo.; Barbara A. Piper, W. Palm Beach, Fla.

[73] Assignee: Alcon Laboratories, Inc., Fort Worth, Tex.

[ * ] Notice: This patent issued on a continued prosecution application filed under 37 CFR 1.53(d), and is subject to the twenty year patent term provisions of 35 U.S.C. 154(a)(2).

[ * ] Notice: The term of this patent shall not extend beyond the expiration date of Pat. No. 5,603,774.

[21] Appl. No.: 732,591

[22] Filed: Oct. 15, 1996

Related U.S. Application Data

[63] Continuation of Ser. No. 570,370, Dec. 11, 1995, Pat. No. 5,603,774, which is a continuation of Ser. No. 358,042, Dec. 15, 1994, abandoned, which is a continuation of Ser. No. 127,224, Sep. 27, 1993, abandoned, filed as PCT/US93/04080 Apr. 30, 1993..

[51] Int. Cl.⁶ .............................. B08B 3/12; B08B 7/02
[52] U.S. Cl. .................................................. 134/1; 134/42
[58] Field of Search ................... 134/1, 42; 204/192.35, 204/192.36; 422/23

[56] References Cited

U.S. PATENT DOCUMENTS

| | | | |
|---|---|---|---|
| 4,312,575 | 1/1982 | Peyman et al. | 351/160 |
| 4,740,282 | 4/1988 | Gesser et al. | 204/165 |
| 5,578,079 | 11/1996 | Kamel et al. | 623/6 |
| 5,603,774 | 2/1997 | LeBoeuf et al. | 134/1 |

FOREIGN PATENT DOCUMENTS

| | | |
|---|---|---|
| A-51279/90 | 9/1990 | Australia . |
| 0 379 146 A2 | 1/1990 | European Pat. Off. . |
| 0 487 418A | 5/1992 | European Pat. Off. . |
| 59-24825 | 2/1984 | Japan . |
| 59-71336 | 4/1984 | Japan . |
| 64-24835 | 1/1989 | Japan . |
| HEI 1-299560 | 12/1989 | Japan . |
| 2-84444 | 3/1990 | Japan . |
| HEI 3-128060 | 5/1991 | Japan . |
| 3-286832 | 12/1991 | Japan . |
| 2 051 827 | 1/1981 | United Kingdom . |
| WO 92/00708 | 1/1992 | WIPO . |
| WO 92/05694 | 4/1992 | WIPO . |
| WO 92/05696 | 4/1992 | WIPO . |

OTHER PUBLICATIONS

Brennan, "Surface Modification of Polyethylene Fibres for Enhanced Performance in Composites," Trends in Polymer Science, vol. 3, No. 1 (1995).

Hall et al., "Activated Gas Plasma Surface Treatment of Polymers for Adhesive Bonding," *J. Appl. Polymer Science* 13:2085–2096 (1969).

Hettlich et al., "Plasma–induced surface modifications on silicone intraocular lenses: chemical analysis and in vitro characterization," *Biomaterials*, 12:521–524 (Jul., 1991).

Chung–Peng Ho et al., "Modification of Silicone Contact Lenses by Plasma Polymerization and Subsequent Plasma Treatments," PMSE vol. 56:705–709 (1987).

Chung–Peng Ho, B.; "Ultrathin Coating by Methane Plasma Polymerization Applied to Silicone Rubber Contact Lenses," Master of Science Thesis, University of Missouri–Rolla (1986).

Chung–Peng Ho et al., "Ultrathin coating of plasma polymer of methane applied on the surface of silicone contact lenses," *J. of Biomedical Materials Research*, 22:919–937 (1988).

N. Inagaki et al., "Distribution of Polymer Deposition in Glow Discharge Polymerization in a Capacitively Coupled System," *J. of Applie Polymer Science*, 26:3425–3433 (1981).

N. Inagaki et al., "Adhesion of Glow Discharge Polymers in Metals and Polymers," *J. of Applied Polymer Science*, 26:3333–3341 (1981).

Tidwell, C.D., "The Development of a Surface–Modified, Self–Passivating Intraocular Lens," Master of Science Thesis, University of Washington (1990).

*Primary Examiner*—Zeinab El-Arini
*Attorney, Agent, or Firm*—Patrick M. Ryan

[57] ABSTRACT

The tackiness associated with certain soft acrylic polymers can be reduced by plasma treatment of the polymer surface. This is particularly useful with regard to intraocular lenses (IOLs), especially foldable IOLs, which are made from such soft acrylic polymers.

10 Claims, No Drawings

METHOD FOR REDUCING TACINESS OF SOFT ACRYLIC POLYMERS

This is a continuation of U.S. patent application Ser. No. 08/570,370 filed Dec. 11, 1995, now U.S. Pat. No. 5,603,774 which is a Continuation of U.S. Ser. No. 08/358,042 filed Dec. 15, 1994, now abandoned, which is a Continuation of Ser. No. 08/127,224 filed Sep. 27, 1993, now abandoned which is a national stage application of PCT/US93/04080 filed Apr. 30, 1993.

BACKGROUND OF THE INVENTION

The present invention relates to a method for reducing the tackiness of certain soft acrylic polymers. The present invention is particularly useful in relation to ophthalmic lenses made of such soft acrylic polymers, especially foldable intraocular lenses.

Intraocular lenses have been known since about 1950. They are used to replace the natural lenses of eyes which have been damaged by trauma or disease, such as cataracts. A typical intraocular lens (IOL) comprises an artificial lens ("optic") and at least one support member ("haptic") for positioning the IOL in the eye. The optic may be formed from any of a number of different materials, including polymethylmethacrylate (PMMA), and it may be hard, relatively flexible or even fully deformable in order to permit the IOL to be rolled or folded and inserted through a relatively small incision in the eye. The haptic is generally made of some resilient material, such as polypropylene or PMMA. The IOLs can have either a "one-piece" or a "multi-piece" design. A multipiece lens is so called because the optic and the haptic(s) are made separately and then the haptics are attached to the optic. In a one-piece lens, the optic and haptic(s) are formed out of one piece of material, and depending on the material, the haptics are then cut, or lathed, out of the material to produce the IOL.

European Patent Publication No. 485 197 A1 (published 13 May 1992) discloses a class of soft acrylic polymers which are suitable for forming IOLs which have high refractive index, are flexible and transparent, can be inserted into the eye through a relatively small incision and recover their original shape after insertion. Although this type of lens material is advantageous in that thinner lenses may be crafted, which allow the IOLs to be folded and permit the use of smaller incisions, it has been found that this type of lens material has a tendency to adhere to itself, as well as to the handling tools. In fact, the inserted IOL can take several minutes to release from itself following insertion. A tacky lens requires more manipulations by the surgeon and increases surgery time (because of the manipulations and lengthy unfolding time). The reduced surface tack lens can be more easily manipulated during surgical implantation. The final outcome with a reduced surface tack lens is easier IOL placement, reduced surgery time, and greater safety for the patient.

Both chemically non-reactive and chemically reactive plasmas have been used to treat various polymer surfaces for several years. See, for example: Inagaki et al., "Adhesion of Glow Discharge Polymers to Metals and Polymers," *Journal of Applied Polymer Science* 26:3333–3341 (1981), and Inagaki et al., "Distribution of Polymer Deposition in Glow Discharge Polymerization in a Capacitively Coupled System," *Journal of Applied Polymer Science,* 26:3425–3433 (1981). In addition, plasma treatments have recently been used to treat silicone contact lenses and silicone intraocular lenses. See, for example: Ho et al., "Ultrathin Coating of Plasma Polymer of Methane Applied on the Surface of Silicone Contact Lenses," *Journal of Biomedical Materials Research,* 22:919–937 (1988); Hettlich et al., "Plasma-induced Surface Modifications on Silicone Intraocular Lenses: Chemical Analysis and In Vitro Characterization," *Biomaterials,* 12:521–524 (1991); and Tidwell, C. D., "The Development of a Surface-modified, Self-passivating Intraocular Lens," Master of Science Thesis, University of Washington (1990).

While plasma treatments have been used to modify other types polymer surfaces, the Applicants are not aware of any prior use of plasma treatments to reduce polymer surface tackiness of soft acrylics.

SUMMARY OF THE INVENTION

It has now surprisingly been found that plasma treatment of the polymer surface of articles made from soft acrylic polymers greatly reduces the tackiness often associated with such articles.

The method of the present invention involves placing the article to be treated into a radio frequency (RF) plasma reactor and treated with a plasma. The plasma may be formed from an inert gas or organic molecules. The conditions for formation of a stable plasma vary from reactor to reactor. The process parameters which are adjusted to create the plasma are: gas type, power, pressure, flow rate, time, and temperature. Factors which vary from reactor to reactor and can influence plasma process conditions are: reactor chamber geometry/volume (barrel, rectangular or cubic volume), electrode type/geometry/spacing, RF power/frequency, gas flow/pumping system. Other factors which influence the process are the material being treated, loading density of samples, and fixturing.

DETAILED DESCRIPTION OF THE INVENTION

The method of the present invention can be applied to any object made of soft acrylic polymers which have an inherent tackiness in air or in fluid medium, where such tackiness is undesirable. It is preferred to utilize the method of the present invention on the modified soft acrylic polymers which can be formed from monomers having the formula:

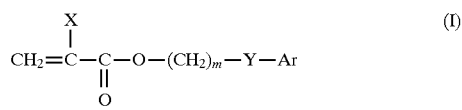

wherein:
X is H or $CH_3$;
m is 0–10;
Y is nothing, O, S, or NR wherein R is H, $CH_3$, $C_nH_{2n+1}$ (n=1–10), iso-$OC_3H_7$, $C_6H_5$, or $CH_2C_6H_5$;
Ar is any aromatic ring, such as benzene, which can be unsubstituted or substituted with H, $CH_3$, $C_2H_5$, n-$C_3H_7$, iso-$C_3H_7$, $OCH_3$, $C_6H_{11}$, Cl, Br, $C_6H_5$ or $CH_2C_6H_5$; and
a cross-linking monomer having a plurality of polymerizable ethylenically unsaturated groups.

European Patent Publication No. 485 197 A1 published 13 May 1992 ("the 197 Application"), discloses methods for preparing these soft acrylic polymers and discusses these polymers in greater detail; therefore, they are not further discussed herein. In addition, the '197 Application discloses methods for forming IOLs from these polymers. The entire contents of the '197 Application are hereby incorporated by reference herein.

Although Applicants do not intend to be bound by any particular theory, Applicants believe that there are three primary mechanisms involved in reducing tackiness of these soft acrylic articles by inert gas plasma treatment:

1) The ionic or charged particle bombardment on the extended polymer chains of the IOL surface create clipped chains (the pendant chemical groups are physically removed by the ion bombardment on the polymer surface), resulting in a smoother surface and therefore less intertwining of these chains when the IOL is contacted to either itself or other surfaces (e.g., instruments).

2) During plasma generation, short wavelength UV radiation is also produced which, under high vacuum, will promote enhanced surface cross-linking of the polymer structure. This higher density cross-linking of the polymer surface will contribute to reduced surface tack.

3) The increase of the surface polymer network structure results in a surface having both enhanced polarity and wetting properties (i.e., a more hydrophilic surface); such properties have been proven to have major impact on the tack properties of soft acrylics when immersed in water.

When using reactive molecules to treat soft acrylics, it is believed that the primary mechanism for tackiness reduction is a function of the properties of the particular polymer and particular gas plasma. For example, with methane gas treatment, the treated polymer is not only highly hydrophobic, but is very highly cross-linked, resulting in a smooth, compact surface which minimizes the potential for surface interactions (i.e., molecular chain entanglement).

It should be noted that, depending on the type of plasma being utilized, the tackiness reduction may only occur when the treated article is in aqueous medium (e.g., in water, saline, or aqueous humor) or is wet (if there is residual water on the polymer surface). For example, the tackiness of IOLs is reduced only in aqueous medium when argon gas plasma is used, but when methane gas plasma is used, tackiness is reduced in air, as well as in aqueous medium.

Plasma chambers which are suitable for use in the present invention are commercially available, for example, from Advanced Plasma Systems, Inc. (St. Petersburg, Fla.), GaSonics/IPC, Inc. (Hayward, Calif.), Plasma Science, Inc. (Foster City, Calif.) and Advanced Surface Technology, Inc. (Billerica, Mass.). A particularly useful plasma chamber is the B-Series Plasma System, available from Advanced Plasma Systems, Inc. ("Advanced Plasma"). Fixtures and/or holders for the articles may be desired in order to ensure equal treatment of the surfaces; such fixtures and holders are also available from Advanced Plasma.

The articles to be treated are placed in appropriate fixtures, if necessary or desirable, and loaded into the plasma chamber. The chamber is evacuated, and gas is then introduced into the chamber and adjusted to the desired pressure. The RF power generator is then turned on. A plasma forms within the chamber and is allowed to treat the articles for the desired length of time. After treatment is complete, the RF power generator is turned off and the articles removed from the chamber.

The processing conditions for plasma treatment of soft acrylic articles will vary depending on the plasma type and reactor specifications. In general, the types of plasmas useful in the present invention include inert gases such as argon and helium (and mixtures thereof), as well as reactive gases, such as various hydrocarbons (e.g., methane). For treating soft acrylic IOLs, it is preferred to use argon plasma. For the argon plasma process, the preferred range of process conditions (using a cubic reactor having primary electrodes) are as follows: power=300–400 watts; pressure=150–225 milliTorr (mTorr); and time=3–5 minutes. These settings are approximate only and may vary somewhat, depending on the individual reactor chambers used.

The following examples are presented to illustrate further various aspects of the present invention, but are not intended to limit the scope of the invention in any respect.

EXAMPLE 1

The following is an example of a typical procedure for Argon plasma treatment of soft acrylic optics.

The lens holder and plasma chamber were first cleaned with an oxygen plasma according to procedures well known to those skilled in the art. The optics to be treated were loaded onto the lens holder and the lens holder placed into the plasma chamber. The chamber was then sealed and evacuated. Argon gas was pumped into the chamber until the pressure reached 160 milliTorr ("mTorr"). The RF power generator was then turned on to 400 watts for 5 minutes, at which time the power was turned off. The gas was allowed to flow for 5 minutes after the power was turned off, then the chamber was purged with Argon gas and vacuum broken to atmospheric pressure. Samples were then removed from the chamber.

EXAMPLE 2

In another typical example of Argon plasma treatment of soft acrylic optics, the procedure of Example 1 was followed, except that the chamber was filled with Argon gas to a pressure of 225 mTorr, and the power was applied at 300 watts for a period of 3 minutes.

EXAMPLE 3

In a typical procedure for methane plasma treatment of soft acrylic optics, the procedure of Example 1 was followed, except that the chamber was filled with methane gas to a pressure of 50 mTorr, and the power of 50 watts was applied for a period of 10 minutes.

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

What is claimed is:

1. A method for reducing surface tackiness of a soft acrylic article which has an inherent tackiness in air or fluid medium, said method consisting essentially of the steps of:

placing said soft acrylic article to be treated into a radio frequency plasma reactor chamber;

closing said reactor chamber and reducing pressure within said reactor chamber to substantially zero;

introducing a hydrocarbon plasma gas into said reactor chamber, and adjusting the pressure therein;

creating a plasma within said reactor chamber using a radio-frequency power generator; and treating said soft acrylic article for a time sufficient to reduce the surface tackiness of said soft acrylic article.

2. The method of claim 1, wherein the plasma gas comprises methane.

3. The method of claim 1, wherein said soft acrylic article is placed in an appropriate fixture to ensure equal treatment of the article's surface's prior to being placed into said reactor chamber.

4. The method of claim 3, wherein said soft acrylic article is an intraocular lens, and said appropriate fixture is a lens holder.

5. The method of claim 4, wherein the plasma gas comprises methane.

6. A method for reducing surface tackiness of a soft acrylic intraocular lens which has an inherent tackiness in air or fluid medium, said method consisting essentially of the steps of:

placing said intraocular lens in a lens holder;

placing said intraocular lens and lens holder into a radio frequency plasma reactor chamber;

closing said reactor chamber and reducing pressure within said reactor chamber to substantially zero;

introducing methane gas into said reactor chamber, and adjusting the pressure therein;

creating a plasma within said reactor chamber using a radio-frequency power generator; and treating said intraocular lens for a time sufficient to reduce the surface tackiness of said intraocular lens.

7. The method of claim 6, wherein said reactor chamber is a cubic reactor chamber having primary electrodes.

8. The method of claim 7, wherein after introducing methane gas into said reactor chamber, said reactor chamber's pressure is adjusted to a pressure of about 150 to about 225 milliTorr, and said intraocular lens is treated for a period of about 3 to about 5 minutes.

9. A method for reducing surface tackiness of a soft acrylic article which has an inherent tackiness in air or fluid medium, said method consisting essentially of the steps of:

placing said soft acrylic article to be treated into a radio frequency plasma reactor chamber;

introducing a hydrocarbon plasma gas into said reactor chamber;

creating a plasma within said reactor chamber using a radio-frequency power generator; and treating said soft acrylic article for a time sufficient to remove or substantially reduce the surface tackiness of said soft acrylic article.

10. The method of claim 9 wherein the soft acrylic article is an intraocular lens.

* * * * *